(12) United States Patent
Gustavsson

(10) Patent No.: US 6,881,706 B1
(45) Date of Patent: *Apr. 19, 2005

(54) USE OF A QUATERNARY AMMONIUM GLYCOSIDE SURFACTANT AS AN ADJUVANT FOR FERTILIZERS OR PESTICIDES

(75) Inventor: Bodil Gustavsson, Stora Höga (SE)

(73) Assignee: Akzo Nobel N.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/914,283

(22) PCT Filed: Feb. 10, 2000

(86) PCT No.: PCT/SE00/00261

§ 371 (c)(1),
(2), (4) Date: Aug. 24, 2001

(87) PCT Pub. No.: WO00/49870

PCT Pub. Date: Aug. 31, 2000

(30) Foreign Application Priority Data

Feb. 24, 1999 (SE) .............................. 9900638

(51) Int. Cl.$^7$ .............................................. A01N 57/18
(52) U.S. Cl. ..................... 504/201; 71/64.01; 424/405; 514/114
(58) Field of Search ................................ 504/116, 103, 504/206, 175, 201; 424/405; 514/25, 53, 118, 114; 71/64.01, 904

(56) References Cited

U.S. PATENT DOCUMENTS 5,317,003 A    5/1994 Kassebaum et al. ........ 504/116

6,503,880 B1 * 1/2003 Skold et al. ................. 510/470

FOREIGN PATENT DOCUMENTS

| EP | 0 274 369 | 7/1988 | .......... A01N/57/20 |
| EP | 0 498 145 | 8/1992 | .......... A01N/57/20 |
| WO | WO 96/20203 | 7/1996 | .......... C07H/15/04 |
| WO | WO 98/15181 | 4/1998 | .......... A01N/57/20 |
| WO | WO 98/39273 | 9/1998 | .......... C05G/3/06 |
| WO | WO 99/10462 | 3/1999 | .......... C11D/1/62 |

OTHER PUBLICATIONS

Chemical Abstract JP50543403, Feb. 1993.

Patents Abstract vol. 16 No. 518, C–999 JP 4–193891, Jul. 1992.

* cited by examiner

Primary Examiner—Neil S. Levy
(74) Attorney, Agent, or Firm—Ralph J. Mancini

(57) ABSTRACT

The present invention relates to the use of a quaternary ammonium glycoside surfactant as an adjuvant for fertilizers or pesticides, such as herbicides. The surfactant contains at least one hydrocarbon group with 6–24 carbon atoms and at least one quaternary ammonium group where at least one substituent is an alkyleneoxy containing group which is connected to a saccharide residue by a glycosidic bond. Also compositions containing pesticides or fertilizers are described. These quaternary ammonium glycoside surfactants have an essentially improved biodegradability. They also improve the uptake and efficacy of fertilizers and herbicides.

19 Claims, No Drawings

USE OF A QUATERNARY AMMONIUM GLYCOSIDE SURFACTANT AS AN ADJUVANT FOR FERTILIZERS OR PESTICIDES

The present invention was filed on Feb. 10, 2000 under the Patent Cooperation Treaty as International Application No. PCT/SE00/00261, and claims priority of Swedish application No. 9900638-9 filed on Feb. 24, 1999.

The present invention relates to the use of a quaternary ammonium glycoside surfactant as an adjuvant for fertilisers or pesticide s, such as herbicides. The surfactants are obtained from ethoxylated quaternary ammonium compounds and reducing saccharides or alkyl glycosides, and the cationic part of the molecule is connected to the sugar residue by a glycosidic bond.

It is well known that both the uptake and efficacy of many fertilisers and pesticides can be improved by the addition of other compounds, adjuvants, and many surfactants have been used for this purpose. The mechanism for their action is complex, and the effect is not only caused by an improved wetting of the leaf surface.

Also the addition of ammonium sulphate to pesticides may improve their efficacy. Many of these formulations are not shelf stable, and must be prepared in place by tank-mixing the pesticide with the ammonium sulphate. However, the addition of surfactants may also be of help in these instances, and compositions containing both a pesticide and ammonium sulphate can acquire an improved stability by the presence of certain surfactants.

It is also an advantage if the adjuvants do not generate a lot of foam when formulations containing pesticides or fertilisers are produced, or when they are applied by spraying.

The most widely used surfactant in commercial formulations containing the well-known herbicide glyphosate (glyphosate=N-(phosphonomethyl)glycine) is an ethoxylated fatty amine. Many more kinds of surfactants have been used as adjuvants for pesticides, and among them quaternary ammonium salts have been described. For example in U.S. Pat. No. 5,317,003 and EP-B1-0 274 369 herbicidal compositions containing glyphosate and quaternary ammonium salts are claimed. In U.S. Pat. No. 5,317,003 a herbicidal composition comprising glyphosate salts and an ethoxylated/propoxylated quaternary ammonium surfactant is described, where the weight ratio of surfactant to glyphosate is between about 1:5 to 5:1. This composition is claimed to be non-irritant to the eyes, of low toxicity to aquatic life, and of similar efficacy as the best commercial glyphosate formulations. The solutions are also claimed to be clear and stable. In the above-mentioned EP-B1-0 274 369 the compositions also contain ammonium sulphate. In this case the quaternary ammonium salt makes a longer shelf life possible is for these herbicidal compositions. However, both the amine ethoxylates and the quaternary ammonium surfactants suffer from the drawback that they are not readily biodegradable.

Surfactants containing sugar residues and nonionic, anionic or cationic groups are known by the publication JP 93-043403. These surfactants are used in pesticide formulations. The ionic part of the molecules described in JP 93-043403 is connected to the sugar residue by an ether bond, which originates from a nonglycosidic hydroxyl substituent on the sugar. This means that the ionic group is not a part of the glycosidic group that contains a large hydrocarbon residue.

In JP 4-193891 cationic sugar surfactants where the cationic part is connected to the sugar residue by a glycosidic bond are described for use as surfactants.

The WO 99/10462 discloses the use of quaternary ammonium glycosides of the same type as in JP 4-193891 as hydrotropes for surfactants.

The purpose of the present invention is to provide adjuvants for pesticide formulations and for formulations containing fertilisers, that are more effective than conventional quaternary ammonium surfactants. Another purpose is to provide adjuvants with an improved biodegradability compared to prior known quaternary ammonium compounds used as adjuvants.

These purposes can be achieved by using a quaternary ammonium glycoside surfactant containing at least one hydrocarbon group with 6–24 carbon atoms and at least one quaternary ammonium group where at least one substituent is an alkyleneoxy containing group which is connected to a saccharide residue by a glycosidic bond. Preferably the substituent has the formula $(AO)_s(G)_p$ where AO is an alkyleneoxy group with 2–4 carbon atoms, G is a saccharide residue, p is a number from 1 to 10 and s is a number from 1 to 15. These quaternary ammonium glycoside surfactants differ from the above-mentioned ethoxylated quaternary ammonium surfactants in that a greater portion of the alkoxylated part of the molecule is exchanged for sugar residues. The quaternary ammonium glycoside surfactants are disclosed as such in the above-mentioned documents JP 4-193891 and WO 99/10462.

Suitable quaternary ammonium glycoside surfactants according to the invention have the formula

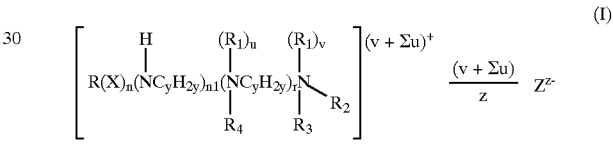

where R is an aliphatic group with 6–24, preferably 8–20 carbon atoms; $R_1$ is an aliphatic group with 1–4 carbon atoms or $(AO)_s(G)_p$; $R_2$, $R_3$ and $R_4$ independently are a group $(AO)_s(G)_p$, an aliphatic group with 1–24 carbon atoms or a hydroxyalkyl group with 2–4 carbon atoms; AO is an alkyleneoxy group with 2–4 carbon atoms; s is 0–15, preferably 1–6 and $\Sigma$ s=1–30, preferably 3–15; G is a saccharide residue which is connected to the rest of the molecule by a glycosidic bond and p (the degree of polymerisation) is 0–10 and $\Sigma$ p=1–20; r=0–3; y=2–3; X=CO or $COO(AO)_t(C_qH_{2q})$ or $O(AO)_t(C_qH_{2q})$; n=0 or 1; $n_1$ is 0 except when X is CO, then $n_1$ is 1; q=2–4; t=0–4; u=0 or 1 and v=0 or 1, provided that the sum (v+$\Sigma$ u) is 1–3, preferably 1; Z is an anion, preferably a monovalent anion, such as $Cl^-$ or methyl sulphate and z is the charge of the anion Z. The nitrogen atoms where u or v is 1 are quaternary and thus have a permanent positive charge. These quaternary ammonium glycoside surfactants have, in comparison with prior known quaternary ammonium surfactants that have been used as adjuvants, an essentially improved biodegradability. When using the quaternary ammonium glycoside surfactants in formulations containing pesticides, such as herbicides, for example glyphosate, the activity of the herbicide is enhanced more than when using the corresponding quaternary ammonium surfactants in the formulations, when comparing activity related to the molar amount of quaternary nitrogen present in the formulations. Also shelf stable formulations containing ammonium sulphate can be obtained when using the quaternary ammonium glycoside surfactants as adjuvants, and these formulations exhibit still larger herbicidal effects. Another advantage when using these glycosides in herbicidal formulations is that highly concentrated formulations can be obtained. At high concentrations of herbicides most other adjuvants either cause gelling or give rise to highly viscous formulations, whereas formulations containing the quaternary ammonium glycosides remain clear and of a low viscosity. For instance, a formulation in water containing 40.7% a.e. of glyphosate isopropylamine salt and 8.3% by weight of 3-aminopropyl $C_8$–$C_{10}$-alkyl ether+5 EO that has been quaternised and glucosidised was totally clear and of low viscosity. This makes it easy to dilute the solution to the desired concentration just before use. An additional benefit of these compounds is their foaming behaviour. Many of the quaternary ammonium glycosides according to the present invention are rather low-foaming compounds, and the foam they are generating collapses quickly.

In formulations containing an active amount of the quaternary ammonium glycosides as an adjuvant, the amount of glycoside can vary within wide limits, but is normally from 10% to 500% by weight calculated on the amount of pesticide or fertiliser present in the formulation, preferably between 20% to 200%.

The product (I) can be produced by reacting a) a reducing saccharide or an alkyl glycoside and b) a quaternary ammonium compound having the formula

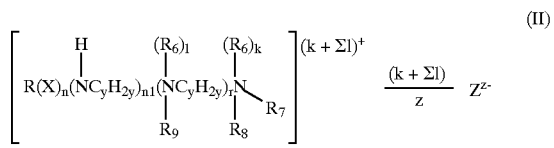

(II)

where $R_6$ is independently an aliphatic group with 1–4 carbon atoms or —$CH_2CH_2OH$; $R_7$, $R_8$ and $R_9$ independently are a group $(AO)_s$, an aliphatic group with 1–24 carbon atoms or a hydroxyalkyl group with 2–4 carbon atoms; l=0 or 1 and k=0 or 1, provided that the sum (k+Σl) is 1–3, preferably 1; and R, AO, s, X, n, $n_1$, y, r, Z and z have the same meaning as in formula I. The nitrogen atoms where k or l is 1 are quaternary and thus have a permanent positive charge. The obtained reaction mixture contains essential amounts of both the quaternary ammonium glycoside surfactant I and the quaternary ammonium compound II. This product mixture can advantageously be used without any purification as an adjuvant. Normally the weight ratio between the quaternary ammonium glycoside surfactant I and the quaternary ammonium compound II is from 1:3 to 9:1.

Suitable examples of the quaternary ammonium glycoside surfactants and the quaternary ammonium compounds are those having the formulae

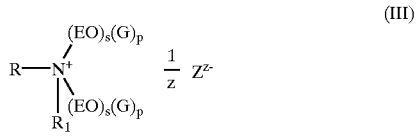

(III)

where R is an aliphatic group with 6–24, preferably 8–20 carbon atoms; $R_1$ is an aliphatic group with 1–4 carbon atoms or the group $C_2H_4O(G)_p$; G is a saccharide residue that is connected to the polyethyleneoxy chain by a glycosidic bond and p (the degree of polymerisation) is 0–10, preferably 0–5, Σ p being 1–15, preferably 1–8; EO is an ethyleneoxy group; s is 0–12; Σ s is 2–15, preferably 4–12; Z and z have the meaning mentioned in formula I and

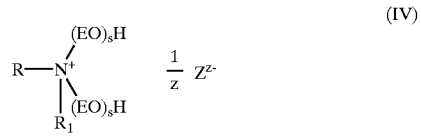

(IV)

where R, $R_1$, EO, Z, z and s have the same meaning as in formula III except that p in the group $R_1$ is 0, respectively.

Other preferred examples of the quaternary ammonium glycosides are compounds according to formula I where $X=O(AO)t$ $(C_qH_{2q})$ where q is 3; n=1; r=0 and v=1, that are present in a mixture with quaternary ammonium compounds according to formula II where $X=O(AO)_t(C_qH_{2q})$ where q is 3; n=1; r=0; and k=1, in a weight ratio 1:3–9:1.

Further preferred examples of quaternary ammonium glycosides are compounds according to formula I where n=0; $n_1$=0; r=1; y=3; u=1 and v=1, that are present in a mixture with quaternary ammonium compounds according to formula II, where n=0; $n_1$=0; r=1; y=3; k=1 and l=1, in a weight ratio 1:3–9:1.

Suitable examples of hydrophobic groups R in formula 1–IV are hexyl, 2-ethylhexyl, octyl, decyl, cocoalkyl, lauryl, oleyl, rapeseed alkyl and tallow alkyl.

The production of these surfactants is described in WO 99/10462, where the procedure below is used.

The process involves the reaction between
a) an amine compound containing at least one hydrocarbon group with 6–24 carbon atoms and at least one quaternary ammonium group, where at least one substituent is a hydroxyalkyl containing group, and
b) a reducing saccharide or an alkyl glycoside where the alkyl group has 1–8 carbon atoms, at least partially in the presence of an acid.

The process described is a glycosidation or a transglycosidation reaction.

Quaternary ammonium glycosides III are easily produced by reacting a reducing saccharide and the quaternary ammonium compound of formula IV. Both of these starting materials are easily available. The reaction mixtures containing essential amounts of both compound III and IV are preferably used as adjuvants without any separation of the compounds, mainly because such a separation is a costly operation. The relation between quaternary ammonium glycoside surfactant and the quaternary ammonium compound could vary between 1:3 and 9:1, preferably between 2:3 and 9:1. The two other preferred groups of quaternary ammonium glycosides are also easily prepared by the same method. The quaternary ammonium compounds that are used as starting materials in these cases are ethoxylated and quaternised 3-aminopropyl alkyl ethers and ethoxylated and diquaternised alkyl-1,3-diaminopropanes respectively. These compounds are also easily available, and the products resulting after the glucosidation reaction function well as adjuvants for pesticides and fertilisers.

In JP 41-193891 another method for producing quaternary ammonium glycosides is described, which involves a glycosidation reaction with a polyalkyleneglycol halohydrin. The intermediate product could then be reacted with a tertiary amine, yielding a quaternary product. To remove unreacted polyalkyleneglycol halohydrine, the product mixture is then purified by distillation or solvent extraction.

The quaternary ammonium glycosides could be added as adjuvants to both liquid, such as aqueous, and solid agricultural compositions containing pesticides such as herbicides, acaricides, fungicides, insecticides, as well as plant growth regulators and fertilisers. Typical examples of herbicides are different amine salts of glyphosate, such as the isopropylamine salt, the dimethylamine salt and the ethylenediamine salt; glufosinate, salts of 2,4-dichlorophenoxyacetic acid, salts of 4-chloro-2-S methylphenoxyacetic acid, bialaphos, dicamba, diphenylethers, imidazolinones and sulfonylureas. The preferred pesticides are the water soluble herbicides, and the most preferred herbicide is glyphosate, and the salts thereof.

Other examples of formulations where the quaternary ammonium glycosides may be used as adjuvants are micronutrient solutions containing one or several micronutrients, such as iron, manganese, copper, zinc, boron and molybdenum. The micronutrients may be complexed to e.g. aminocarboxylates, such as EDTA, DTPA, HEDTA, EDDHMA and is EDDHA. In addition to micronutrients and chelating agents, the formulations may also contain macronutrients, such as nitrogen, phosphorus, potassium, magnesium and sulphur, and pesticides may also be included. These above-mentioned formulations are particularly suitable for foliar applications.

The formulations according to the invention may also contain other additives, such as other surfactants, preservatives, additives to further enhance pesticidal activity, such as ammonium sulphate; solvents, corrosion inhibitors, thickeners, sequestering agents, anti-freeze agents, anti-foam agents, anti-gelling agents and dyes.

The compositions could also contain viscosity reducing agents such as glycerol, ethylene glycol, propylene glycol and low molecular weight polyethylene or polypropylene glycols.

The compositions could be concentrates as well as diluted, "ready to use", solutions. The concentrations may vary within wide limits, and a pesticide formulation could contain 0.01–99.9% by weight of a pesticide, 0–40% by weight of ammonium sulphate and an amount of 0.01–70% by weight of a mixture containing quaternary ammonium glycoside surfactant and quaternary ammonium compound present in a weight ratio 1:3–9:1. The preferred pesticide is glyphosate, or a salt thereof, which is preferably present in an amount of 0.02–70% by weight. As a concentrate, the concentrations are normally in the range of 4–70% for the pesticide, 2–50% for the adjuvants and 0–40% of ammonium sulphate, whereas for the ready-to-use solutions the corresponding ranges are 0.01–4%, 0.01–8% and 0–40%. The components could all be mixed in the concentrate or be tank-mixed just before spraying the solution.

A fertiliser formulation could contain 0.0001–99.9%, preferably 0.001–99.9%, by weight of a fertiliser and an amount of 0.0001–70%, preferably 0.001–70%, by weight of a mixture containing quaternary ammonium glycoside surfactant and quaternary ammonium compound present in a weight ratio 1:3–9:1. In a ready-to-use formulation the concentration of micronutrients are usually in the lower area of the range.

The following examples are illustrative of the invention and are not to be construed as a limitation of the scope.

EXAMPLE 1

Biodegradability tests were performed with the "closed bottle test" as described in OECD Test 301D. 2-Ethylhexylamine that had been alkoxylated with 2 moles of propylene oxide and 4 moles of ethylene oxide, and then quaternised by methyl chloride, was compared to the glucosidised product of the same compound. After 28 days the glucosidised product had reached 43% biodegradation, whereas the unglucosidised product had only reached 11% biodegradation. Although the glucosidised product contained about 15% of unreacted quaternary ammonium compound, the biodegradation of the glucosidised product mixture was almost 4 times as fast as that of the unglucosidised product.

EXAMPLE 2

The herbicidal effects of formulations containing the herbicide glyphosate and quaternary ammonium glycosides according to the present invention were investigated in greenhouse tests. For comparison, formulations containing some of the corresponding quaternary ammonium compounds were included in the investigation.

Roundup® (a commercially available herbicidal standard formulation from Monsanto), which contains the isopropylamine salt of glyphosate and an ethoxylated fatty amine, was also included as a reference. In Roundup® the weight ratio adjuvant/glyphosate is 1:2.

The weeds used were glasshouse grown Coachgrass (*Elymus repens*), Winter Oil Seed Rape (*Brassica napus*) and Rigid Ryegrass (*Lolium rigidum*). The treatments for *Elymus repens* and *Brassica napus* were sprayed at three dose rates; 0.15, 0.25 and 0.7:5 kg a.e./ha referring to glyphosate, and for *Lolium rigidum* the doses were 0.08, 0.15 and 0.25 kg a.e./ha referring to glyphosate. The recommended dose rate for glyphosate is 1.08 kg a.e./ha. There were three replicates of each treatment.

The aqueous herbicide formulations were sprayed on the plants by using a laboratory track sprayer fitted with an 80015E flat fan nozzle, at a spray pressure of 210 kPA delivering 202 liters/ha.

The following formulation recipe was used for the greenhouse tests displayed in Tables 1–6. These formulations were diluted with water before spraying.

Formulation (Concentrated)

| | |
|---|---|
| Glyphosate isopropyl-amine salt | 13.8% w/w a.e. |
| Cationic adjuvant | 6.9% w/w |
| Water | balance |

To test the stability all concentrated formulations were kept at 0° C. and at 54° C. for two weeks. The solutions were still clear and homogenous after that time.

The diluted solutions that were sprayed had the concentrations displayed in the table below.

| Dose rate (kg/ha) | Concentration of glyphosate acid equivalents (%) | Concentration of adjuvant (%) |
|---|---|---|
| 0.75 | 0.37 | 0.18 |
| 0.25 | 0.12 | 0.06 |
| 0.15 | 0.07 | 0.04 |
| 0.08 | 0.04 | 0.02 |

The experiments were assessed according to the amount of green life growth and regrowth 6 weeks after spraying. A score of 0–100% was used, where 100% is a totally dead plant, and for example a 50% reduction in the amount of green growth present was scored by a comparison to the best untreated plant, the latter scoring 0%. Since the glucosidised quaternary compounds by necessity contain a lower weight content of quaternary nitrogen as compared to the corresponding quaternary ammonium compounds, an activity index was formed. The activity index is calculated by dividing the effect obtained by the number of moles of quaternary nitrogen per ha contained in the different formulations.

All products have been quaternised by methyl chloride.

TABLE 1

Greenhouse test with *Brassica napus*. The dose rates are referring to the amount of glyphosate, the amount of cationic adjuvant being half of that amount.

| Product | Moles of quaternary nitrogen per ha | Effect (%) | Activity index (effect/mole) |
|---|---|---|---|
| 2-ethylhexylamine + 8EO, quaternised | | | |
| (0.75 kg/ha) | 0.705 | 92 | 130 |
| (0.25 kg/ha) | 0.235 | 43 | 183 |
| (0.15 kg/ha) | 0.141 | 12 | 85 |
| 2-ethylhexylamine + 8EO, quaternised and glucosidised | | | |
| (0.75 kg/ha) | 0.368 | 73 | 198 |
| (0.25 kg/ha) | 0.123 | 37 | 300 |
| (0.15 kg/ha) | 0.074 | 12 | 162 |
| 2-ethylhexylamine + 2PO + 4EO, quaternised | | | |
| (0.75 kg/ha) | 0.794 | 90 | 113 |
| (0.25 kg/ha) | 0.265 | 50 | 189 |
| (0.15 kg/ha) | 0.159 | 20 | 126 |
| 2-ethylhexylamine + 2PO + 4EO, quaternised and glucosidised | | | |
| (0.75 kg/ha) | 0.391 | 97 | 248 |
| (0.25 kg/ha) | 0.130 | 47 | 361 |
| (0.15 kg/ha) | 0.078 | 13 | 167 |
| n-octylamine + 8EO, quaternised | | | |
| (0.75 kg/ha) | 0.705 | 95 | 135 |
| (0.25 kg/ha) | 0.235 | 45 | 191 |
| (0.15 kg/ha) | 0.141 | 8 | 57 |
| n-octylamine + 8EO, quaternised and glucosidised | | | |
| (0.75 kg/ha) | 0.368 | 93 | 253 |
| (0.25 kg/ha) | 0.123 | 35 | 285 |
| (0.15 kg/ha) | 0.074 | 12 | 162 |
| n-octylamine + 2PO + 4EO, quaternised | | | |
| (0.75 kg/ha) | 0.794 | 85 | 107 |
| (0.25 kg/ha) | 0.265 | 47 | 177 |
| (0.15 kg/ha) | 0.159 | 5 | 31 |
| n-octylamine + 2PO + 4EO, quaternised and glucosidised | | | |
| (0.75 kg/ha) | 0.391 | 95 | 242 |
| (0.25 kg/ha) | 0.130 | 50 | 385 |
| (0.15 kg/ha) | 0.078 | 17 | 218 |

TABLE 2

Greenhouse test with *Lolium rigidum*. The dose rates are referring to the amount of glyphosate, the amount of cationic adjuvant being half of that amount.

| Product | Moles of quaternary nitrogen per ha | Effect (%) | Activity index (effect/mole) |
|---|---|---|---|
| 2-ethylhexylamine + 8EO, quaternised | | | |
| (0.25 kg/ha) | 0.235 | 95 | 404 |
| (0.15 kg/ha) | 0.141 | 65 | 461 |
| (0.08 kg/ha) | 0.075 | 33 | 440 |
| 2-ethylhexylamine + 8EO, quaternised and glucosidised | | | |
| (0.25 kg/ha) | 0.123 | 85 | 691 |
| (0.15 kg/ha) | 0.074 | 68 | 919 |
| (0.08 kg/ha) | 0.039 | 28 | 718 |
| 2-ethylhexylamine + 2PO + 4EO, quaternised | | | |
| (0.25 kg/ha) | 0.265 | 90 | 340 |
| (0.15 kg/ha) | 0.159 | 67 | 421 |
| (0.08 kg/ha) | 0.085 | 27 | 318 |
| 2-ethylhexylamine + 2PO + 4EO, quaternised and glucosidised | | | |
| (0.25 kg/ha) | 0.130 | 90 | 692 |
| (0.15 kg/ha) | 0.078 | 50 | 641 |
| (0.08 kg/ha) | 0.042 | 48 | 1143 |
| n-octylamine + 8EO, quaternised | | | |
| (0.25 kg/ha) | 0.235 | 92 | 391 |
| (0.15 kg/ha) | 0.141 | 72 | 511 |
| (0.08 kg/ha) | 0.075 | 40 | 533 |
| n-octylamine + 8EO, quaternised and glucosidised | | | |
| (0.25 kg/ha) | 0.123 | 93 | 756 |
| (0.15 kg/ha) | 0.074 | 53 | 716 |
| (0.08 kg/ha) | 0.039 | 17 | 436 |
| n-octylamine + 2PO + 4EO, quaternised | | | |
| (0.25 kg/ha) | 0.265 | 97 | 366 |
| (0.15 kg/ha) | 0.159 | 60 | 377 |
| (0.08 kg/ha) | 0.085 | 40 | 471 |
| n-octylamine + 2PO + 4EO, quaternised and glucosidised | | | |
| (0.25 kg/ha) | 0.130 | 92 | 708 |
| (0.15 kg/ha) | 0.078 | 62 | 795 |
| (0.08 kg/ha) | 0.042 | 33 | 785 |

TABLE 3

Greenhouse test with *Elymus repens*. The dose rates are referring to the amount of glyphosate, the amount of cationic adjuvant being half of that amount.

| Product | Moles of quaternary nitrogen per ha | Effect (%) | Activity index (effect/mole) |
|---|---|---|---|
| 2-ethylhexylamine + 8EO, quaternised | | | |
| (0.75 kg/ha) | 0.705 | 93 | 132 |
| (0.25 kg/ha) | 0.235 | 73 | 311 |
| (0.15 kg/ha) | 0.141 | 60 | 426 |
| 2-ethylhexylamine + 8EO, quaternised and glucosidised | | | |
| (0.75 kg/ha) | 0.368 | 97 | 264 |
| (0.25 kg/ha) | 0.123 | 67 | 545 |
| (0.15 kg/ha) | 0.074 | 47 | 635 |
| 2-ethylhexylamine + 2PO + 4EO, quaternised | | | |
| (0.75 kg/ha) | 0.794 | 95 | 120 |
| (0.25 kg/ha) | 0.265 | 65 | 245 |
| (0.15 kg/ha) | 0.159 | 37 | 233 |
| 2-ethylhexylamine + 2PO + 4EO, quaternised and glucosidised | | | |
| (0.75 kg/ha) | 0.391 | 92 | 235 |
| (0.25 kg/ha) | 0.130 | 65 | 500 |
| (0.15 kg/ha) | 0.078 | 45 | 576 |
| n-octylamine + 8EO, quaternised | | | |
| (0.75 kg/ha) | 0.705 | 97 | 138 |
| (0.25 kg/ha) | 0.235 | 73 | 311 |
| (0.15 kg/ha) | 0.141 | 53 | 376 |
| n-octylamine + 8EO, quaternised and glucosidised | | | |
| (0.75 kg/ha) | 0.368 | 92 | 250 |
| (0.25 kg/ha) | 0.123 | 75 | 610 |
| (0.15 kg/ha) | 0.074 | 62 | 838 |
| n-octylamine + 2PO + 4EO, quaternised | | | |
| (0.75 kg/ha) | 0.794 | 93 | 117 |
| (0.25 kg/ha) | 0.265 | 68 | 257 |
| (0.15 kg/ha) | 0.159 | 52 | 327 |
| n-octylamine + 2PO + 4EO, quaternised and glucosidised | | | |
| (0.75 kg/ha) | 0.391 | 97 | 248 |
| (0.25 kg/ha) | 0.130 | 72 | 554 |
| (0.15 kg/ha) | 0.078 | 63 | 808 |

TABLE 4

Greenhouse test with *Brassica napus*. The dose rates are referring to the amount of glyphosate, the amount of cationic adjuvant being half of that amount.

| Product | Effect (%) |
|---|---|
| 3-aminopropyl $C_8$–$C_{10}$-alkyl ether + 5EO, quaternised and glucosidised | |
| (0.75 kg/ha) | 97 |
| (0.25 kg/ha) | 45 |
| (0.15 kg/ha) | 10 |
| N-tallow-1,3-propylenediamine + 12EO, quaternised and glucosidised | |
| (0.75 kg/ha) | 100 |
| (0.25 kg/ha) | 48 |
| (0.15 kg/ha) | 18 |
| Roundup ® | |
| (0.75 kg/ha) | 100 |
| (0.25 kg/ha) | 33 |
| (0.15 kg/ha) | 25 |

TABLE 5

Greenhouse test with *Lolium rigidum*. The dose rates are referring to the amount of glyphosate, the amount of cationic adjuvant being half of that amount.

| Product | Effect (%) |
|---|---|
| 3-aminopropyl $C_8$–$C_{10}$-alkyl ether + 5EO, quaternised and glucosidised | |
| (0.25 kg/ha) | 92 |
| (0.15 kg/ha) | 92 |
| (0.08 kg/ha) | 72 |
| N-tallow-1,3-propylenediamine + 12EO, quaternised and glucosidised | |
| (0.25 kg/ha) | 100 |
| (0.15 kg/ha) | 95 |
| (0.08 kg/ha) | 57 |
| Roundup ® | |
| (0.25 kg/ha) | 98 |
| (0.15 kg/ha) | 93 |
| (0.08 kg/ha) | 22 |

TABLE 6

Greenhouse test with *Elymus repens*. The dose rates are referring to the amount of glyphosate, the amount of cationic adjuvant being half of that amount.

| Product | Effect (%) |
|---|---|
| 3-aminopropyl $C_8$–$C_{10}$-alkyl ether + 5EO, quaternised and glucosidised | |
| (0.75 kg/ha) | 93 |
| (0.25 kg/ha) | 75 |
| (0.15 kg/ha) | 62 |
| N-tallow-1,3-propylenediamine + 12EO, quaternised and glucosidised | |
| (0.75 kg/ha) | 93 |
| (0.25 kg/ha) | 70 |
| (0.15 kg/ha) | 52 |
| Roundup ® | |
| (0.75 kg/ha) | 93 |
| (0.25 kg/ha) | 65 |
| (0.15 kg/ha) | 42 |

As is shown from the tables, the quaternary ammonium glucosides according to the present invention are more efficient adjuvants for the herbicide than the corresponding unglucosidised quaternary ammonium compounds that are used as starting materials for the glucosides, when the compounds are compared on a molar basis. The formulations based on the quaternary ammonium glucosides also exhibit comparable or better herbicidal efficacy than the Roundup formulation.

EXAMPLE 3

Some of the quaternary ammonium glucosides according to the present invention were also investigated as adjuvants in the presence of ammonium sulphate. These formulations were compared to the corresponding formulations containing no ammonium sulphate.

Roundup® was used as a reference. In Roundup® the ratio adjuvant/glyphosate is 1:2. It is not possible to add ammonium sulphate to Roundup®, because that makes the product to turn into a gel.

The weeds used were glasshouse grown Coachgrass (*Elymus repens*), Winter Oil Seed Rape (*Brassica napus*) and Rigid Ryegrass (*Lolium rigidum*). The treatments were sprayed at the dose rates 0.25 (for *Lolium rigidum* and *Elymus repens*) and 0.75 kg a.e./ha (for *Brassica napus*); the dose rates referring to glyphosate. There were three replicates of each treatment.

| Formulations with ammonium sulphate | |
|---|---|
| Formulation A | |
| Glyphosate isopropyl-amine salt | 13.8% w/w a.e. |
| Cationic adjuvant | 13.8% w/w |
| Ammonium sulphate | 15% w/w |
| Water | balance |
| Formulation B | |
| Glyphosate isopropyl-amine salt | 13.8% w/w a.e. |
| Cationic adjuvant | 6.9% w/w |
| Ammonium sulphate | 15% w/w |
| Water | balance |
| Formulations without ammonium sulphate | |
| Formulation C | |
| Glyphosate isopropyl-amine salt | 13.8% w/w a.e. |
| Cationic adjuvant | 13.8% w/w |
| Water | balance |
| Formulation D | |
| Glyphosate isopropyl-amine salt | 13.8% w/w a.e. |
| Cationic adjuvant | 6.9% w/w |
| Water | balance |

The stability of the formulations was tested by keeping them for two weeks at 0 and 54° C. All the solutions were still clear and homogeneous after that time. The diluted solutions that were sprayed had the concentrations displayed in the table below.

| Formulation | Dose rate (kg/ha) | Conc. of Glyphosate acid equiv. (%) | Conc. Of ammonium sulphate (%) | Conc. of adjuvant (%) |
|---|---|---|---|---|
| A | 0.75 | 0.37 | 0.40 | 0.37 |
| B | 0.75 | 0.37 | 0.40 | 0.18 |
| C | 0.75 | 0.37 | 0 | 0.37 |
| D | 0.75 | 0.37 | 0 | 0.18 |
| A | 0.25 | 0.12 | 0.13 | 0.12 |
| B | 0.25 | 0.12 | 0.13 | 0.06 |
| C | 0.25 | 0.12 | 0 | 0.12 |
| D | 0.25 | 0.12 | 0 | 0.06 |

The experiments were assessed for the amount of green live growth and regrowth 6 weeks after spraying for *Brassica napus* and *Lolium rigidum* and 8 weeks after spraying for *Elymus repens*. A score of 1–10 was used, where 0=dead, 5=50% reduction in the amount of green growth present in comparison with the best untreated and 10=as best untreated.

TABLE 7

Greenhouse test with *Brassica napus*. The dose rate is 0.75 kg a.e./ha, referring to the amount of glyphosate.

| Product | Effect (score 0–10) |
|---|---|
| Cocoamine + 4EO, quaternised and glucosidised. | |
| Formulation C (no ammonium sulphate) | 1.7 |
| Formulation A (with ammonium sulphate) | 0.0 |
| Cocoamine + 6EO, quaternised and glucosidised. | |
| Formulation C (no ammonium sulphate) | 2.7 |
| Formulation A (with ammonium sulphate) | 0.0 |
| Cocoamine + 4EO, quaternised and glucosidised. | |
| Formulation D (no ammonium sulphate) | 2.3 |
| Formulation B (with ammonium sulphate) | 0.0 |
| Cocoamine + 6EO, quaternised and glucosidised. | |
| Formulation D (no ammonium sulphate) | 3.0 |
| Formulation B (with ammonium sulphate) | 2.0 |
| Roundup ® | 1.2 |

TABLE 8

Greenhouse test with *Lolium rigidum*. The dose rate is 0.25 kg a.e./ha, referring to the amount of glyphosate.

| Product | Effect (score 0–10) |
|---|---|
| Cocoamine + 4EO, quaternised and glucosidised. | |
| Formulation C (no ammonium sulphate) | 0.0 |
| Formulation A (with ammonium sulphate) | 0.0 |
| Cocoamine + 6EO, quaternised and glucosidised. | |
| Formulation C (no ammonium sulphate) | 0.0 |
| Formulation A (with ammonium sulphate) | 0.0 |
| Cocoamine + 4EO, quaternised and glucosidised. | |
| Formulation D (no ammonium sulphate) | 1.0 |
| Formulation B (with ammonium sulphate) | 0.0 |

TABLE 8-continued

Greenhouse test with *Lolium rigidum*. The dose rate is 0.25 kg a.e./ha, referring to the amount of glyphosate.

| Product | Effect (score 0–10) |
|---|---|
| Cocoamine + 6EO, quaternised and glucosidised, | |
| Formulation D (no ammonium sulphate) | 0.3 |
| Formulation B (with ammonium sulphate) | 0.0 |
| Roundup ® | 0.3 |

TABLE 9

Greenhouse test with *Elymus repens*. The dose rate is 0.25 kg a.e./ha, referring to the amount of glyphosate.

| Product | Effect (score 0–10) |
|---|---|
| Cocoamine + 4EO, quaternised and glucosidised. | |
| Formulation C (no ammonium sulphate) | 0.0 |
| Formulation A (with ammonium sulphate) | 0.0 |
| Cocoamine + 6EO, quaternised and glucosidised. | |
| Formulation C (no ammonium sulphate) | 0.7 |
| Formulation A (with ammonium sulphate) | 0.3 |
| Cocoamine + 4EO, quaternised and glucosidised. | |
| Formulation D (no ammonium sulphate) | 1.3 |
| Formulation B (with ammonium sulphate) | 0.3 |
| Cocoamine + 6EO, quaternised and glucosidised. | |
| Formulation D (no ammonium sulphate) | 0.7 |
| Formulation B (with ammonium sulphate) | 0.3 |
| Roundup ® | 0.3 |

The examples show that the addition of ammonium sulphate further enhances the herbicidal activity of the formulations. The best results were obtained with formulations containing ammonium sulphate and where the weight ratio between adjuvant and glyphosate was 1:1.

EXAMPLE 4

Foam height measurements were performed according to the standard Ross Miles procedure. The foam height was measured immediately; and after 5 minutes. The test was made at 50° C. using 0.05% (w/w) surfactant solutions. The glucosidised products are compared to the corresponding unglucosidised quaternary ammonium compounds. The adjuvant used in Roundup® is also included as a reference.

TABLE 10

Foam height measurements.

| Product | Foam height (mm) after 0 min | Foam height (mm) after 5 min |
|---|---|---|
| 2-ethylhexylamine + 8EO, quaternised | 15 | 0 |
| 2-ethylhexylamine + 8EO, quaternised and glucosidised | 13 | 0 |
| 2-ethylhexylamine + 2PO + 4EO, quaternised | 6 | 0 |
| 2-ethylhexylamine + 2PO + 4EO, quaternised and glucosidised | 3[1] | 0 |
| n-octylamine + 8EO, quaternised | 45 | 4 |
| n-octylamine + 8EO, quaternised and glucosidised | 35 | 3 |
| n-octylamine + 2PO + 4EO, quaternised | 7 | 0 |
| n-octylamine + 2PO + 4EO, quaternised and glucosidised | 8[1] | 0 |
| Tallowamine ethoxylate (adjuvant in Roundup ®) | 95 | 5 |

[1]The foam collapses after 3 s

The quaternary ammonium glucosides are more low-foaming than the corresponding quaternary ammonium compounds, and much more low-foaming than the adjuvant used in Roundup®. The foam that the glucosides generate collapses quickly, in some instances almost instantaneously.

What is claimed is:

1. An adjuvant for pesticides or fertilizers which comprises at least one quaternary ammonium glycoside surfactant containing at least one hydrocarbon group with 6–24 carbon atoms and at least one quaternary ammonium group where at least one substituent is an alkyleneoxy containing group which is connected to a saccharide residue by a glycosidic bond.

2. The adjuvant of claim 1 wherein in said quaternary ammonium glycoside surfactant, the substituent has the formula $(AO)_s(G)_p$, where AO is an alkyleneoxy group with 2–4 carbon atoms, G is a saccharide residue, p is a number from 1 to 10 and s is a number from 1–15.

3. The adjuvant of claim 1 wherein said quaternary ammonium glycoside surfactant has the formula

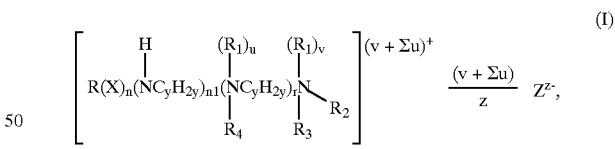

(I)

where R is an aliphatic group with 6–24 carbon atoms; $R_1$ is an aliphatic group with 1–4 carbon atoms or $(AO)_s(G)_p$; $R_2$, $R_3$ and $R_4$ independently are a group $(AO)_s(G)_p$, an aliphatic group with 1–24 carbon atoms or a hydroxyalkyl group with 2–4 carbon atoms; AO is an alkyleneoxy group with 2–4 carbon atoms; s is 0–15 and $\Sigma$ s=1–30; G is a saccharide residue which is connected to the rest of the molecule by a glycosidic bond and the degree of polymerisation p is 0–10; $\Sigma$ p=1–20; r=0–3; y=2–3; X=CO or $COO(AO)_t(C_qH_{2q})$ or $O(AO)_t(C_qH_{2q})$; n=0 or 1; $n_1$ is 0 except when X is CO, then $n_1$ is 1; q=2–4; t=0–4; u=0 or 1 and v=0 or 1, provided that the sum (v+$\Sigma$ u) is 1–3; Z is an anion and z is the charge of the anion Z.

4. The adjuvant of claim 3 comprising a quaternary ammonium glycoside surfactant and which further comprises a quaternary ammonium compound having the formula

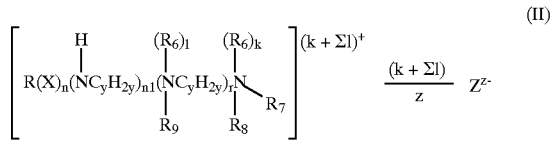
(II)

where $R_6$ is independently an aliphatic group with 1–4 carbon atoms or —$CH_2CH_2OH$; $R_7$, $R_8$, and $R_9$ independently are a group $(AO)_s$, an aliphatic group with 1–24 carbon atoms or a hydroxyalkyl group with 2–4 carbon atoms; l=0 or 1 and k=0 or 1, provided that the sum (k+Σ l) is 1–3; and R, AO, s, X, n, $n_1$, y, r, Z and z have the same meaning as in claim 3, in a weight ratio 1:3–9:1.

5. The adjuvant composition of claim 3, where the quaternary ammonium glycoside surfactant has the formula

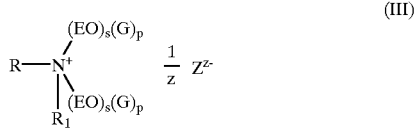
(III)

where R is an aliphatic group with 6–24 carbon atoms; $R_1$ is an aliphatic group with 1–4 carbon atoms or the group $C_2H_4O(G)_p$; G is a saccharide residue that is connected to the polyethyleneoxy chain by a glycosidic bond and p (the degree of polymerisation) is 0–10; Σ p is 1–15; EO is an ethyleneoxy group; s is 0–12; Σ s is 2–15; Z and z have the meaning mentioned in formula I in claim 3.

6. The adjuvant of claim 5, where the quaternary ammonium glycoside surfactant is present in a mixture with a quaternary ammonium compound having the formula

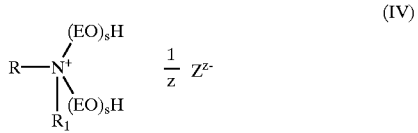
(IV)

where R, $R_1$ EO, Z, z and s, have the same meaning as in formula III in claim 5, except that p in the group $R_1$ is 0, in a weight ratio 1:3–9:1.

7. The adjuvant of claim 3, where $X=O(AO)_r(C_qH_{2q})$ where q is 3; n=1; r=0 and v=1.

8. The adjuvant of claim 7 which comprises a quaternary ammonium glycoside and which further comprises a quaternary ammonium compound of the formula

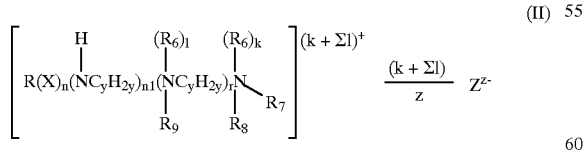
(II)

where $R_6$ is independently an aliphatic group with 1–4 carbon atoms or —$CH_2CH_2OH$; $R_7$, $R_8$, and $R_9$ independently are a group $(AO)_s$, an aliphatic group with 1–24 carbon atoms or a hydroxyalkyl group with 2–4 carbon atoms; l=0 or 1 and k=1, provided that the sum (k+Σ l) is 1–3; R is an aliphatic group with 6–24 carbon atoms; AO is an alkyleneoxy group with 2–4 carbon atoms; s is 0–15; $n_1$ is 0 except when X is CO, then $n_1$ is 1; y=2–3; Z is an anion and z is the charge of the anion Z $X=O(AO)_r(C_qH_{2q})$ where q is 3; n=1; and r=0, wherein the weight ratio of said quaternary ammonium glycoside and said quaternary ammonium compound is 1:3–9:1.

9. The adjuvant of claim 3, where n=0; $n_1$=0; r=1; y=3; u=1 and v=1.

10. The adjuvant of claim 9, which comprises, in addition to said quaternary ammonium glycoside, a quaternary ammonium compound of the formula

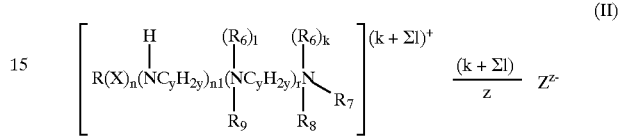
(II)

where $R_6$ is independently an aliphatic group with 1–4 carbon atoms or —$CH_2CH_2OH$; $R_7$, $R_8$, and $R_9$ independently are a group $(AO)_s$, an aliphatic group with 1–24 carbon atoms or a hydroxyalkyl group with 2–4 carbon atoms; l=1 and k=1, provided that the sum (k+Σ l) is 1–3; R is an aliphatic group with 6–24 carbon atoms; AO is an alkyleneoxy group with 2–4 carbon atoms; s is 0–15; $n_1$ is 0; y=3; Z is an anion and z is the charge of the anion Z $X=O(AO)_r(C_qH_{2q})$ where q is 3; n=0; and r=1; wherein the weight ratio of said quaternary ammonium glycoside and said quaternary ammonium compound is 1:3–9:1.

11. The adjuvant of claim 1 wherein said pesticide is a herbicide.

12. The adjuvant of claim 11 wherein said herbicide is glyphosate or a salt thereof.

13. A pesticide formulation which comprises at least one pesticide and an active amount of a quaternary ammonium glycoside surfactant according to claim 1.

14. The pesticide formulation of claim 13 wherein the amount of quaternary ammonium glycoside surfactant is between 20–200% by weight calculated on the amount of pesticide present in the formulation.

15. The pesticide formulation of claim 13, which contains 0.01–99.9% by weight of a pesticide, 0–40% by weight of ammonium sulphate and an amount of 0.01–70% by weight of by weight of an adjuvant, wherein said adjuvant comprises:

i) at least one quaternary ammonium glycoside surfactant of the formula

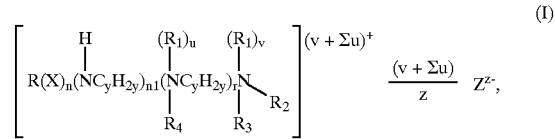
(I)

where R is an aliphatic group with 6–24 carbon atoms; $R_1$ is an aliphatic group with 1–4 carbon atoms or $(AO)_s(G)_p$; $R_2$, $R_3$ and $R_4$ independently are a group $(AO)_s(G)_p$, an aliphatic group with 1–24 carbon atoms or a hydroxyalkyl group with 2–4 carbon atoms; AO is an alkyleneoxy group with 2–4 carbon atoms; s is 0–15 and Σ s=1–30; G is a saccharide residue which is connected to the rest of the molecule by a glycosidic bond and the degree of polymerisation p is 0–10; Σ p=1–20; r=0–3; y=2–3; X=CO or $COO(AO)_r(C_qH_{2q})$ or $O(AO)_r(C_qH_{2q})$; n=0 or 1; $n_1$ is 0 except when X is CO, then $n_1$ is 1; q=2–4; t=0–4; u=0 or 1 and v=0 or 1, provided that the sum (v+Σ u) is 1–3; Z is an anion and z is the charge of the anion Z; and ii) at least one quaternary ammonium compound of the formula

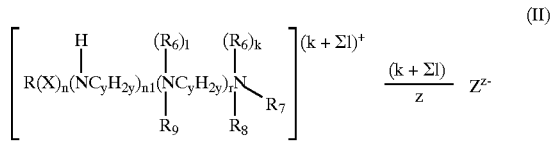

(II)

where $R_6$ is independently an aliphatic group with 1–4 carbon atoms or —$CH_2CH_2OH$; $R_7$, $R_8$, and $R_9$ independently are a group $(AO)_s$, an aliphatic group with 1–24 carbon atoms or a hydroxyalkyl group with 2–4 carbon atoms; l=0 or 1 and k=0 or 1, provided that the sum (k+Σ l) is 1–3; R is an aliphatic group with 6–24 carbon atoms, AO is an alkyleneoxy group with 2–4 carbon atoms; s is 0–15 and Σ s=1–30; X=CO or $COO(AO)_t(C_qH_{2q})$ or $O(AO)_t(C_qH_{2q})$; n=0 or 1; $n_1$ is 0 except when X is CO, then $n_1$ is 1; r=0–3; y=2–3; Z is an anion and z is the charge of the anion Z; wherein the weight ratio of I) to ii) is 1:3–9:1.

16. The formulation of claim 15, wherein the formulation is in liquid form and that the pesticide is glyphosate or a salt thereof, which is present in an amount of 0.02–70% by weight.

17. A fertilizer formulation which comprises at least one fertilizer and an active amount of a quaternary ammonium glycoside surfactant according to claim 1.

18. The fertilizer formulation of claim 17 which comprises 0.0001–99.9% by weight of a fertilizer and an amount of 0.0001–70% by weight of an adjuvant, wherein said adjuvant comprises:

i) at least one quaternary ammonium glycoside surfactant of the formula

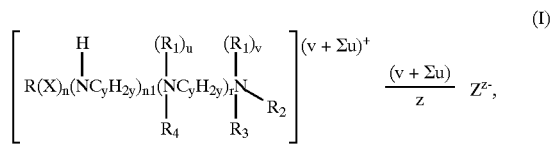

(I)

where R is an aliphatic group with 6–24 carbon atoms; $R_1$ is an aliphatic group with 1–4 carbon atoms or $(AO)_s(G)_p$;

$R_2$, $R_3$ and $R_4$ independently are a group $(AO)_s(G)_p$, an aliphatic group with 1–24 carbon atoms or a hydroxyalkyl group with 2–4 carbon atoms; AO is an alkyleneoxy group with 2–4 carbon atoms; s is 0–15 and Σ s=1–30; G is a saccharide residue which is connected to the rest of the molecule by a glycosidic bond and the degree of polymerisation p is 0–10; Σ p=1–20; r=0–3; y=2–3; X=CO or $COO(AO)_t(C_qH_{2q})$ or $O(AO)_t(C_qH_{2q})$; n=0 or 1; $n_1$ is 0 except when X is CO, then $n_1$ is 1; q=2–4; t=0–4; u=0 or 1 and v=0 or 1, provided that the sum (v+Σ u) is 1–3; Z is an anion and z is the charge of the anion Z; and ii) at least one quaternary ammonium compound of the formula

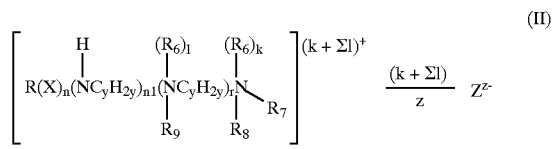

(II)

where $R_6$ is independently an aliphatic group with 1–4 carbon atoms or —$CH_2CH_2OH$; $R_7$, $R_8$, and $R_9$ independently are a group $(AO)_s$, an aliphatic group with 1–24 carbon atoms or a hydroxyalkyl group with 2–4 carbon atoms; l=0 or 1 and k=0 or 1, provided that the sum (k+Σ l) is 1–3; R is an aliphatic group with 6–24 carbon atoms, AO is an alkyleneoxy group with 2–4 carbon atoms; s is 0–15 and Σ s=1–30; X=CO or $COO(AO)_t(C_qH_{2q})$ or $O(AO)_t(C_qH_{2q})$; n=0 or 1; $n_1$ is 0 except when X is CO, then $n_1$ is 1; r=0–3; y=2–3; Z is an anion and z is the charge of the anion Z; wherein the weight ratio of I) to ii) is 1:3–9:1.

19. The fertilizer formulation of claim 17 wherein the amount of quaternary ammonium glycoside surfactant is between 20–200% by weight calculated on the amount of fertilizer present in the formulation.

* * * * *